(12) United States Patent
Thakkar

(10) Patent No.: US 9,913,873 B2
(45) Date of Patent: Mar. 13, 2018

(54) TURMERIC EXTRACT CONTAINING SOFT PASTILLES

(71) Applicant: Jatin Vasant Thakkar, Mumbai (IN)

(72) Inventor: Jatin Vasant Thakkar, Mumbai (IN)

( * ) Notice: Subject to any disclaimer, the term of this patent is extended or adjusted under 35 U.S.C. 154(b) by 126 days.

(21) Appl. No.: 15/026,844

(22) PCT Filed: Oct. 31, 2014

(86) PCT No.: PCT/IN2014/000697
§ 371 (c)(1),
(2) Date: Apr. 1, 2016

(87) PCT Pub. No.: WO2015/075745
PCT Pub. Date: May 28, 2015

(65) Prior Publication Data
US 2016/0235803 A1 Aug. 18, 2016

(30) Foreign Application Priority Data
Nov. 2, 2013 (IN) .......................... 1590/MUM/2013

(51) Int. Cl.
*A61K 36/00* (2006.01)
*A61K 36/9066* (2006.01)
*A61K 9/00* (2006.01)
*A61K 47/10* (2017.01)
*A61K 47/42* (2017.01)
*A61J 3/06* (2006.01)
*A61K 31/12* (2006.01)
*A61K 31/715* (2006.01)
*A61K 47/24* (2006.01)

(52) U.S. Cl.
CPC ............. *A61K 36/9066* (2013.01); *A61J 3/06* (2013.01); *A61K 9/0056* (2013.01); *A61K 31/12* (2013.01); *A61K 31/715* (2013.01); *A61K 47/10* (2013.01); *A61K 47/24* (2013.01); *A61K 47/42* (2013.01)

(58) Field of Classification Search
CPC ...................................... A61K 36/00
See application file for complete search history.

(56) References Cited

U.S. PATENT DOCUMENTS

| | | |
|---|---|---|
| 2003/0021752 A1 | 1/2003 | Whittle et al. |
| 2005/0123632 A1 | 6/2005 | Chen et al. |
| 2006/0147989 A1* | 7/2006 | Rosenbloom .......... A61K 36/82 435/6.14 |
| 2011/0200670 A1 | 8/2011 | Thakkar |

FOREIGN PATENT DOCUMENTS

WO 2012163937 A2 12/2012

* cited by examiner

*Primary Examiner* — Qiuwen Mi
(74) *Attorney, Agent, or Firm* — The Roy Gross Law Firm, LLC; Roy Gross

(57) ABSTRACT

The present disclosure provides a soft pastille containing turmeric extract as an active ingredient. The pastille is prepared using at least one gelling agent and at least one plasticizer in combination with pharmaceutically acceptable excipients, wherein the ratio of the gelling agent to the plasticizer is in a range of 1:2.5 to 1:3.3.

15 Claims, 1 Drawing Sheet

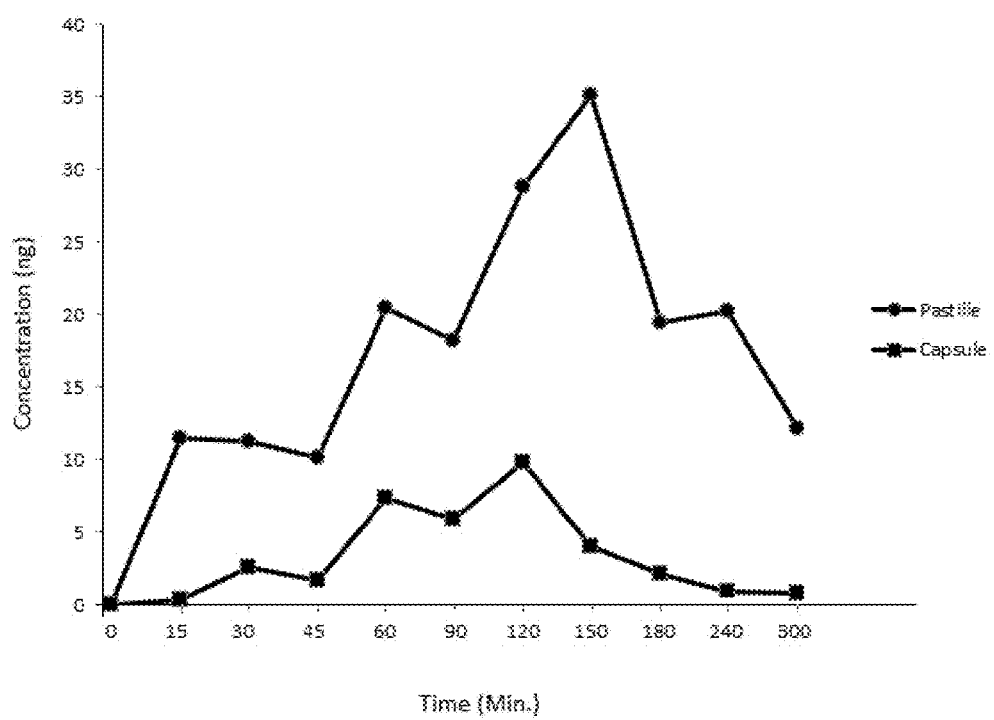

TURMERIC EXTRACT CONTAINING SOFT PASTILLES

FIELD OF THE DISCLOSURE

The present disclosure relates to an oral medicament. The present disclosure particularly, relates to an oral medicament in the form of a soft pastille.

BACKGROUND

Among the various routes of drug administration, an oral route remains the preferred route for the administration of therapeutic agents due to low cost, ease of administration and high level of patient compliance. However, hepatic first pass metabolism and drug degradation within a gastrointestinal (GI) tract significantly prohibits an oral administration of certain classes of drugs. Consequently, other absorptive mucosae are being considered as potential sites for drug administration including the mucosal linings of the nasal, rectal, vaginal, ocular, and oral cavity. These transmucosal routes of drug delivery offer distinct advantages over a peroral administration for systemic drug delivery, such as possible bypass of the first pass effect and avoidance of pre-systemic elimination within the GI tract.

However, drug delivery through an oral cavity is considered to be a promising alternative, due to its unique physiological features and high patient compliance. Various dosage forms like solutions, lozenges, pastilles, chewing gums, sprays, patches, films, hydrogels, hollow fibres and microspheres are available for drug delivery through the oral cavity.

The majority of the commercially available formulations for drug delivery through the oral cavity are solid dosage forms such as lozenges and pastilles.

Lozenges and pastilles are solid preparations that are intended to dissolve or disintegrate slowly in the mouth. They contain one or more medicaments usually in a flavored and sweetened base. These are most often used for localized effects in the mouth but can also be used for systemic effect if the drug is well absorbed through the buccal lining. The drugs which can be successfully delivered to the site of its action through this route include analgesics, anesthetics, antiseptics, antimicrobials, antitussives, anti-nausants, antacids and decongestants.

However, high sugar content is a major drawback associated with lozenges and pastilles prepared by conventional methods. Further, lozenges get break down into pieces followed by accidental swallowing which in turn results in excessive transfer of active ingredient in GI tract. Furthermore, it is not comfortable for a patient to keep a hard product like lozenges in the buccal cavity for a prolonged period.

Curcumin is diarylheptanoid and principal curcuminoid of the popular Indian spice turmeric (*Curcuma longa*). The other two curcuminoids are desmethoxycurcumin and bis-desmethoxycurcumin. The curcuminoids are natural phenols that are responsible for the yellow color of turmeric. Curcumin is insoluble in water and is impermeable through the cell membrane. Traditionally, curcumin is commonly utilized in many therapeutic remedies, either alone or in conjunction with other natural substances. Accumulated evidence indicates that curcumin is associated with a great variety of pharmacological activities, such as anti-inflammatory, and antioxidant activities.

Curcumin acts by way of modulating multiple molecular targets, cell signaling proteins, cell cycle proteins, cytokines and chemokines, enzymes, receptors and cell surface adhesion molecules. It is known that the potential health benefits of curcumin are limited by its poor solubility, low absorption from the gut, rapid metabolism and rapid systemic elimination.

The major portion of ingested curcumin is excreted through the feces un-metabolized whereas the small portion which is absorbed is extensively converted to its water-soluble metabolites, glucuronides and sulfates. Microbial metabolism of curcumin yields dihydrocurcumin, and tetrahydrocurcumin through NADPH dependent reduction. Curcumin and its reduced metabolites are conjugated with monoglucuronide via beta-glucuronidase, a monosulfate via sulfatase enzymes and a mixed sulfate/glucuronide, resulting in curcumin-glucuronoside, dihydocurcumin glucuronoside, tetrahydrocurcumin glucuronoside or corresponding monosulfate and mixed sulfate/glucuronoside. Different formulations have been tried in recent past to improve the absorption of curcumin including nanocrystals, emulsions, liposomes, self-assemblies and nanogels.

Curcumin is suggested as a potent anti-microbial agent however, inadequate emphasis has been given on the development of a dosage form, containing curcumin as an active ingredient having anti-inflammatory activity. Further, available oral dosage forms containing curcumin do not produce desired local and/or systemic action.

Accordingly, it is desirable to provide a palatable, clinically efficacious, well-tolerable and long-acting soft pastille containing curcumin as an active ingredient.

OBJECTS

Some of the objects of the present disclosure which at least one embodiment is adapted to provide, are described herein below:

It is an object of the present disclosure to provide a soft pastille containing turmeric extract.

It is another object of the present disclosure to provide a soft pastille which can continuously deliver the active ingredient/s to affected areas which include but is not limited to the throat, esophagus and gastrointestinal track for a prolonged period of time.

It is yet another object of the present disclosure to provide soft pastilles which are cost effective and palatable.

Other objects and advantages of the present disclosure will be more apparent from the following description, which is not intended to limit the scope of the present disclosure.

SUMMARY

In accordance with the present disclosure there is provided a soft pastille comprising:

turmeric extract in an amount ranging from 0.1 wt. % to 20 wt. % of the mass of the pastille; at least one gelling agent in an amount ranging from 5 wt. % to 40 wt. % of the mass of the pastille; at least one plasticizer in an amount ranging from 30 wt. % to 70 wt. % of the mass of the pastille; at least one sweetener in an amount ranging from 0.05 wt. % to 10 wt. % of the mass of the pastille; at least one releasing agent in an amount ranging from 0.5 wt. % to 30 wt. % of the mass of the pastille; at least one preservative in an amount ranging from 0.05 wt. % to 2 wt. % of the mass of the pastille; at least one flavouring agent in an amount ranging from 0.01 wt. % to 5 wt. % of the mass of the pastille; water in an amount of ranging from 5 wt. % to 20 wt. % of the mass of the pastille; and optionally, at least one pharmaceutically acceptable excipient.

Typically, said pastille being capable of being dissolved in the buccal cavity in about 5 to about 30 minutes, depending on the user's sucking pattern. Typically, the ratio of the gelling agent to the plasticizer is in the range of 1:2.5 to 1:3.3.

Typically, the turmeric extract comprises 5 wt. % to 93 wt. % of curcuminoids, 5 to 30 wt. % of turmeric oil, and 1 to 10 wt. % of polysaccharides.

Typically, the curcuminoids comprise 83 to 95 wt. % of curcumin, 2 to 7 wt. % of desmethoxycurcumin and 1 to 3 wt. % of bis-desmethoxycurcumin In accordance with another aspect there is provided a process for the preparation of soft pastille; said process comprising the following steps:

introducing 30 to 70 wt. % of a plasticizer selected from the group consisting of glycerine, sorbitol and combinations thereof and water in a reactor followed by adding 5 to 40 wt. % of a gelling agent selected from the group consisting of gelatin, carrageenan and mixtures thereof and stirring to obtain a first mixture; heating said first mixture at a temperature ranging from 25° C. to 85° C., preferably at 65 to 85° C. and admixing 0.5 to 30 wt. % of a releasing agent selected from the group consisting of lecithin, oil, starch and combinations thereof and optionally at least one pharmaceutically acceptable excipient to form a second mixture, wherein the ratio of the gelling agent to the plasticizer being in a range of 1:2.5 to 1:3.3;

adding 0.1 to 20 wt. % of turmeric extract into glycerin to obtain slurry and mixing said slurry and the second mixture for 30 to 45 minutes at a speed of 1500 rpm to form a third mixture comprising partly dissolved and partly dispersed turmeric extract;

incorporating 0.05 wt. % to 10 wt. % of at least one sweetener, 0.01 wt. % to 5 wt. % of at least one flavoring agent and 0.05 wt. % to 2 wt. % of at least one preservative into the third mixture to obtain a mass; and filling the mass into the preformed cavities of blister pack to obtain the pastilles.

BRIEF DESCRIPTION OF ACCOMPANYING DRAWING

FIG. 1 illustrates comparative concentration of curcumin in blood at a pre-determined time interval, when administered through the pastille and capsule dosage form.

DESCRIPTION

The present disclosure is directed to a clinically efficacious, well-tolerated, long-acting soft pastille containing turmeric extract as an active ingredient which can produce desired local and/or systemic action. The soft pastille containing turmeric extract prepared in accordance with the present disclosure can be utilized for the management of diseases or disorders which include but are not limited to duodenal and stomach ulcers, gastritis, esophagitis, heartburn, throat infection, Leukoplakia and the like.

It is found that 98% pure curcumin has poor bioavailability. It is also found that the formulation containing pure curcumin does not produce the desired anti-inflammatory activity and anti-bacterial activity. In view of the preliminary findings, the inventor of the present disclosure focused on obtaining a turmeric extract containing specific actives in a specific proportion which may lead to enhancing the desired therapeutic activity. In accordance with the present disclosure it is found that the turmeric extract containing 5-93% of curcuminoids along with other phyto-constituents such as turmeric oil (5-30%) and polysaccharides (1-10%) when formulated in the soft pastille of the present disclosure shows enhanced anti-inflammatory activity and anti-bacterial activity. It is found that the use of a combination of glycerine and gelatin acts as a solvent for curcumin which in-turn contributes to enhance the bioavailability of curcumin significantly.

The soft pastille of the present disclosure mainly contains turmeric extract as an active ingredient; at least one gelling agent; at least one plasticizer; at least one sweetener; at least one releasing agent; at least one preservative; at least one flavouring agent; and water.

In one embodiment, the pastille contains turmeric extract in an amount ranging from 0.1 wt. % to 20 wt. % of the mass of the pastille; at least one gelling agent in an amount ranging from 5 wt. % to 40 wt. % of the mass of the pastille; at least one plasticizer in an amount ranging from 30 wt. % to 70 wt. % of the mass of the pastille; at least one sweetener in an amount ranging from 0.05 wt. % to 10 wt. % of the mass of the pastille; at least one releasing agent in an amount ranging from 0.5 wt. % to 30 wt. % of the mass of the pastille; at least one preservative in an amount ranging from 0.05 wt. % to 2 wt. % of the mass of the pastille; at least one flavouring agent in an amount ranging from 0.01 wt. % to 5 wt. % of the mass of the pastille; water in an amount ranging from 5 wt. % to 20 wt. % of the mass of the pastille and optionally, at least one pharmaceutically acceptable excipient.

The prepared pastille when placed in the mouth provides local anti-bacterial action. Further, it provides systemic antioxidant and anti-inflammatory effects when the active ingredient of the pastille is absorbed through gastrointestinal track. The combination of gelatin and glycerin solubilizes turmeric extract and helps in buccal and sublingual absorption of the actives of turmeric extract which in turn bypass the liver and acidic pH of stomach. Thus, the pastille of the present disclosure delivers curcuminoids present in the turmeric extract directly into blood in its bio-active form.

In the saliva, the pastilles of the present disclosure slowly erode to form a viscous mass containing gelatin, glycerin and turmeric extract in liquefied form. The part of the turmeric extract that remains un-dissolved also solubilizes with the viscous mass. This viscous mass travels through the throat typically in the pharynx and the larynx region where it coats the inner walls of the passages thereby killing the micro-organisms responsible for the upper respiratory tract infections. Further, the peristalsis movement carries the viscous mass along the esophagus into the stomach and the digestive tract. In the intestine, turmeric extract is assimilated and absorbed through the microvilli and enters the blood stream and further gets metabolized in the liver.

It is believed that the turmeric extract present in the viscous mass acts against various bacteria including the *H. pylori* bacterium. It is further believed that the soft pastilles of the present disclosure may also be used to prevent problems of Halitosis (Bad breath).

The turmeric extract (*Curcuma longa* extract) is either alcoholic or hydro-alcoholic extract.

In one embodiment the turmeric extract comprises 5 wt. % to 93 wt. % of curcuminoids and 5 to 30 wt. % of turmeric oil and 1 to 10 wt. % of polysaccharides. In one embodiment the curcuminoids comprise 83 to 95 wt. % of curcumin, 2 to 7 wt. % of desmethoxycurcumin and 1 to 3 wt. % of bis-desmethoxycurcumin.

In one preferred embodiment, the turmeric extract comprises 80 wt. % to 85 wt. % of curcuminoids and 6 to 8 wt. % of turmeric oil and 2 to 4 wt. % of polysaccharides.

In one preferred embodiment the curcuminoids comprise 90 to 94 wt. % of curcumin, 4 to 6 wt. % of desmethoxycurcumin and 1 to 3 wt. % of bis-desmethoxycurcumin.

The turmeric oil mainly comprises turmerone, atlantone and zingiberen. The extract further comprises at least one phyto-constituent selected from the group consisting of curcuminoids, 1,8-cineole, alpha-pinene and alpha-terpineol.

While formulating the pastille having desired active ingredient release profile the inventors conducted several experimental trials to optimize the ratio of gelling agent to plasticizer. The inventor of the present disclosure surprisingly found that when the ratio of gelling agent (gelatin) to plasticizer (glycerin) is kept below 1:2.5, the formed mixture becomes hard and gets stuck in the nozzle. It is also found that when the ratio of gelling agent to glycerin is kept above 1:3.3, the formed mixture becomes less viscous and results in formation of poor quality pastilles. Therefore, the ratio of gelling agent to glycerin for the preparation of soft pastilles is kept in the range of 1:2.5 to 1:3.3.

The gelling agent employed includes but is not limited to gelatin, agar, algin, carrageenan, guar gum, gum arabic, gum ghatti, gum tragacanth, karaya gum, locust bean gum, pectin, and xanthan gum and mixtures thereof. In one of the preferred embodiments of the present disclosure the gelling agent used is gelatin.

The plasticizer is selected from the group consisting of glycerine, sorbitol and mixtures thereof. In one of the preferred embodiments of the present disclosure the plasticizer is glycerine. The gelling agent used in the present pastilles acts to gel the plasticizer which is pre-mixed with a small quantity of water.

The releasing agent employed in the pastilles is selected from the group consisting of lecithin, oil, starch and mixtures thereof. In one of the preferred embodiments of the present disclosure the releasing agent is lecithin. Lecithin used in the present soft pastilles acts as a releasing agent or lubricating agent which prevents the friction (or sticking) between the inner wall of the nozzle and the pastilles. This also helps end user to eject or remove the pastilles smoothly from the preformed cavities of the blister pack.

The other ingredients of the pastilles play dual role, such as, menthol acts as a permeation enhancer and taste masking agent, whereas eucalyptol acts as a decongestant and taste masking agent.

The pharmaceutically acceptable excipients include but are not limited to diluents, disintegrants, binders, surfactants, emulsifiers, colors and the like.

In accordance with another embodiment of the present disclosure turmeric extract is obtained from the rhizomes of *Curcuma longas.*

In accordance with the present disclosure the sweetener includes but is not limited to stevia, aspartame, saccharin, sucralose and combinations thereof; the preservative includes but is not limited to methyl paraben, propyl paraben, sodium methyl paraben, sodium propyl paraben, grape fruit seed extract, sodium benzoate and combinations thereof; and the flavoring agents include, but are not limited to menthol, vanillin, peppermint, spearmint, lemon, mint, strawberry, banana, pineapple, orange, raspberry, eucalyptol, fennel, cinnamon and combinations thereof.

In accordance with one embodiment of the present disclosure, the afore-stated soft pastille further comprises at least one substance derived from the plants which includes but is not limited to *Zingiber officinale* and *Glycyrrhiza glabra*, in an amount ranging from 0.05% to 10% with respect to the total mass of the pastille.

The substance is derived from the plant parts which include but are not limited to leaves, flowers, fruits, seeds, stem, branches, bark, stolons, tubers, roots, rhizomes and combinations thereof. Typically, the substance is in the form selected from the group consisting of extract, granules, powders, oils, solutions, suspensions, emulsions, isolated fractions and semisolids.

In accordance with one embodiment of the present disclosure, soft pastille further comprises at least one cough suppressant.

*Curcuma longa* (Zingiberaceae)

Description: It is a perennial herb with pulpy, orange, tuberous roots.

Synonyms: Turmeric, *curcuma, Curcuma rotunda, Amomum curcuma*, haldi, halad, and haridra.

Geographical origin: It is native to tropical South Asia. China, Pakistan Bangladesh and other Asian countries are the places where turmeric trees are commonly found.

Chemical constituents: Curcumin, demethoxycurcumin, bisdemethoxycurcumin, turmerin, wenyujinlactone A, neolitamone A, zedoarondiol, isozedoarondiol, aerugidiol, curcumol, curdione, (1R,10R)-epoxy-(−)-1,10-dihydrocurdine3 and parviflorene F4 are the common chemical constituents of haridra.

The rhizomes of *Curcuma longa* used for the preparation of turmeric extract in accordance with the present disclosure were collected from Sangali, Maharashtra.

In accordance with another aspect of the present disclosure there is also provided a process for the preparation of a soft pastille. The process involves the following steps:

In the first step, 30 to 70 wt. % of a plasticizer selected from the group consisting of glycerine, sorbitol and combinations thereof and water are introduced in a reactor followed by adding 5 to 40 wt. % of a gelling agent selected from the group consisting of gelatin, carrageenan and mixtures thereof and stirring to obtain a first mixture; heating said first mixture at a temperature ranging from 25° C. to 85° C., preferably at 65 to 85° C. and admixing 0.5 to 30 wt. % of a releasing agent selected from the group consisting of lecithin, oil, starch and combinations thereof, and optionally at least one pharmaceutically acceptable excipient to form a second mixture. The ratio of the gelling agent to the plasticizer is maintained in a range of 1:2.5 to 1:3.3.

In the next step, 0.1 to 20 wt. % of turmeric extract is added into glycerine to obtain slurry. The turmeric extract comprises 5 wt. % to 93 wt. % of curcuminoids, 5 to 30 wt. % of turmeric oil, and 1 to 10 wt. % of polysaccharides. In one embodiment the curcuminoids comprise 83 to 95 wt. % of curcumin, 2 to 7 wt. % of desmethoxycurcumin and 1 to 3 wt. % of bis-desmethoxycurcumin.

In one preferred embodiment the turmeric extract comprises 80 wt. % to 85 wt. % of curcuminoids and 6 to 8 wt. % of turmeric oil and 2 to 4 wt. % of polysaccharides.

In one preferred embodiment the curcuminoids comprise 90 to 94 wt. % of curcumin, 4 to 6 wt. % of desmethoxycurcumin and 1 to 3 wt. % of bis-desmethoxycurcumin.

The obtained slurry and the second mixture are mixed for 30 to 45 minutes at a speed of 1500 rpm to form a third mixture comprising partly dissolved and partly dispersed turmeric extract. Then 0.05 to 10 wt. % of at least one sweetener, 0.01 to 5 wt. % of at least one flavoring agent, and 0.05 to 2 wt. % of at least one preservative are incorporated into the third mixture to obtain a mass. The obtained mass is filled into the preformed cavity of a blister pack. Alternatively, the obtained mass is collected in a container followed by cooling and solidification. The solidified mass is then transferred into a melter followed by adjusting the temperature of mass in the range from 55° C. to 75° C. to obtain a melted mass. Finally, the melted mass is passed through an injector directly into the preformed cavity of a blister pack.

Pastilles having total weight of 100 mg to 2000 mg containing 10 to 200 mg of turmeric extracts are prepared and tested.

Following examples illustrate the invention, but are not intended to limit the scope of the present invention.

Example 1

A soft pastille in accordance with the present invention was prepared with the following composition.

Each pastille (1500 mg) contains:
Turmeric extract: 110 mg
Gelatin: 276 mg
Glycerine: 872 mg
Water: 155 mg
Lecithin: 45 mg
Spearmint: 1 mg
Eucalyptol: 08 mg
Menthol: 10 mg
Sucralose: 4.4 mg
Tween 80: 15 mg
Methyl paraben: 2.4 mg
Propyl paraben: 1.2 mg
Procedure:

In the first step, accurately weighed glycerine and water were introduced in a reactor followed by adding accurately weighed gelatin to obtain a first mixture and stirring. Then the stirred mixture was heated at 60° C. To this heated mixture lecithin and Tween 80 were added to form a second mixture. In the next step, accurately weighed turmeric extract was added to the second mixture and mixed for 30 minutes at a speed of 1500 rpm to form a third mixture. Then accurately weighed quantities of spearmint, eucalyptol, menthol, sucralose, methyl paraben and propyl paraben were incorporated into the third mixture to obtain a mass. The obtained mass was collected in a container followed by cooling and solidification. The solidified mass was then transferred into a melter followed by heating at 75° C. to obtain a melted mass. Finally, the melted mass was passed through an injector directly into the preformed cavity of a blister pack.

Example 2

Each pastille (1500 mg) contains:
Turmeric extract: 110 mg
Gelatin: 305 mg
Glycerine 848 mg
Water: 150 mg
Lecithin: 45 mg
Spearmint: 1 mg
Eucalyptol: 08 mg
Menthol: 10 mg
Sucralose: 4.4 mg
Tween 80: 15 mg
Methyl paraben: 2.4 mg
Propyl paraben: 1.2 mg Example 3

Each pastille (1500 mg) contains:
Turmeric extract: 50 mg
Gelatin: 333 mg
Glycerine: 875 mg
Water: 155 mg
Lecithin: 45 mg
Spearmint: 1 mg
Eucalyptol: 8 mg
Menthol: 10 mg
Sucralose: 4.4 mg
Tween 80: 15 mg
Methyl paraben: 2.4 mg
Propyl paraben: 1.2 mg Example 4

Each pastille (1500 mg) contains:
Turmeric extract: 110 mg
Gelatin: 150 mg
Glycerine: 950 mg
Water: 168 mg
Lecithin: 45 mg
Spearmint: 01 mg
Eucalyptol: 08 mg
Menthol: 10 mg
Sucralose: 4.4 mg
Tween 80: 15 mg
Lactose: 35 mg
Methyl paraben: 2.4 mg
Propyl paraben: 1.2 mg Example 5

Each pastille (1500 mg) contains:
Turmeric extract: 100 mg
Gelatin: 275 mg
Glycerine: 860 mg
Water: 151 mg
Lecithin: 30 mg
Spearmint: 1 mg
Eucalyptol: 8 mg
Menthol: 10 mg
Sucralose: 4.4 mg
Tween 80: 15 mg
Starch: 15 mg
Lactose: 27 mg
Methyl paraben: 2.4 mg
Propyl paraben: 1.2 mg Example 6

Each pastille (1500 mg) contains:
Turmeric extract: 200 mg
Gelatin: 270 mg
Glycerine: 800 mg
Water: 141 mg
Lecithin: 47 mg
Eucalyptol: 8 mg
Spearmint: 1 mg
Menthol: 10 mg
Sucralose: 4.4 mg
Tween 80: 15 mg
Methyl paraben: 2.4 mg
Propyl paraben: 1.2 mg
Efficacy Study:

An open-label trial (open trial) was conducted in 16 subjects suffering from cold and cough. (Open trial is a type of clinical trial in which both the researcher/physician and participant know which treatment is being administered)

Inclusion/Enrollment Criteria:

The subjects/volunteers of age from 8 to 60 years suffering from cold and cough accompanied by at least one of the following symptoms were enrolled in the study.

Fever≥100° F.;

Fever accompanied by sweating, chills and cough;

Swollen glands;

Sinusitis;

Runny nose; and

Constant sneezing

The volunteers who were already being administered other anti-cough medication/anti-histamines and who were suffering with chronic ashthma were not included in the study.

All the enrolled 16 subjects were prescribed soft pastilles of the present disclosure.

Dose Prescribed:

Group I—Age: 8 to 12 yrs: 3 pastilles per day; and

Group II—Age: 12 to 60 yrs: 4-5 pastilles per day.

Dosing period: 1 to 7 days

Follow up was carried out with each subject on a regular basis to check the degree of relief after the administration of present pastilles.

Results:

9 subjects reported complete relief from cold and cough on the second day of the treatment.

2 subjects reported lowering of fever on the second day and complete relief on the third day of the treatment.

3 subjects reported complete relief from cold and cough on the fourth day of the treatment.

2 subjects reported relief from fever and complete relief from cold and cough on the fifth day of the treatment.

The results showed that the pastilles of the present disclosure are highly effective in treating cold and cough in 2 to 5 days of dosage regimen.

A similar study (control study) was conducted in subjects suffering from cold and cough, wherein the enrolled subjects (10) were prescribed the capsule containing turmeric extract. The result showed that the capsule containing turmeric extract were ineffective in treating cold and cough in a period of 5 days. The subjects were then prescribed the pastilles of the present disclosure. The results showed that the pastilles of the present disclosure are highly effective in treating cold and cough in 2 to 5 days.

Furthermore, a comparative study was conducted wherein the capsule containing turmeric extract was compared with the pastille of the present disclosure with respect to blood concentration of curcumin at pre-determined time intervals.

The study was carried out in 11 subjects. The subjects were divided into two groups.

First group (I): 6 subjects (A-E) were administered capsules containing turmeric extract; and Second group (II): 5 subjects (A-E) were administered the pastille of the present disclosure.

The blood samples of each subject were collected at pre-determined time intervals and analyzed for the concentration of curcumin The results are provided herein below in table Nos. 1, 2 and 3

TABLE 1

Concentration of curcumin in blood of subjects after the administration of the present pastilles

| Time (min) | Concentration in ng | | | | |
|---|---|---|---|---|---|
| | A | B | C | D | E |
| 0 | 0 | 0 | 0 | 0 | 0 |
| 15 | 21.98 | 0 | 5.31 | 6.26 | 24.01 |
| 30 | 17.49 | 0 | 5.77 | 6 | 27.05 |
| 45 | 17.74 | 0 | 4.12 | 14.4 | 14.58 |
| 60 | 28.76 | 5.31 | 10.16 | 7.41 | 50.96 |
| 90 | 22.17 | 11.19 | 12.14 | 8.46 | 37.1 |
| 120 | 16.65 | 42.57 | 32.11 | 7.38 | 45.42 |
| 150 | 19.93 | 87.65 | 20.63 | 8.47 | 39.28 |
| 180 | 15.6 | 0 | 10.89 | 11.19 | 59.69 |
| 240 | 21.36 | 0 | 6.55 | 8.51 | 64.92 |
| 300 | 18.32 | 0 | 6.4 | 3.49 | 32.21 |

TABLE 2

Concentration of curcumin in Blood of subjects after the administration of the capsule

| Time (min) | Concentration in ng | | | | |
|---|---|---|---|---|---|
| | A | B | D | E | F |
| 0 | 0 | 0 | 0 | 0 | 0 |
| 15 | 1.85 | 0 | 0 | 0 | 0 |
| 30 | 3.47 | 9.95 | 0 | 0 | 0 |
| 45 | 2.67 | 4.19 | 0 | 0 | 0 |
| 60 | 2.58 | 0 | 13 | 10.42 | 14.78 |
| 90 | 2.13 | 4.67 | 15.01 | 9.07 | 0 |
| 120 | 2.72 | 6.3 | 23.18 | 11.9 | 9.19 |
| 150 | 2.42 | 4.26 | 0 | 9.17 | 0 |
| 180 | 2.09 | 3.1 | 0 | 3.7 | 0 |
| 240 | 0 | 2.49 | 0 | 0 | 0 |
| 300 | 0 | 2.96 | 0 | 0 | 0 |

The average blood concentration at each time interval for pastille and capsule was determined and compared. The results are shown in Table No. 3. and FIG. 1.

TABLE 3

Comparative concentration of curcumin in blood

| Time (min) | Present pastille | Capsule |
|---|---|---|
| | Conc. in ng | |
| 0 | 0 | 0 |
| 15 | 11.51 | 0.31 |
| 30 | 11.26 | 2.53 |
| 45 | 10.16 | 1.66 |
| 60 | 20.52 | 7.33 |
| 90 | 18.21 | 5.89 |
| 120 | 28.83 | 9.74 |
| 150 | 35.19 | 4.05 |
| 180 | 19.47 | 2.16 |
| 240 | 20.27 | 0.87 |
| 300 | 12.08 | 0.82 |

The results clearly indicate that the bioavailability of curcumin is significantly enhanced when administered through the present pastille compared to the conventional capsule formulation. Thus, based on the bioavailability data it can be predicted that the soft pastille of the present disclosure shows enhanced efficacy because of a combination of turmeric extract containing specific actives, a gelling agent and a plasticizer in a specific proportion.

Efficacy of the Present Pastilles was also Studied in Subjects Suffering from Leukoplakia:

Leukoplakia in the mouth or oral leukoplakia is defined as a predominantly white lesion of the oral mucosa. Oral leukoplakia is commonly seen in those who smoke or chew tobacco. Leukoplakia is a premalignant lesion. The chance of transformation into oral squamous cell carcinoma (OSCC, a type of oral cancer) is upto 20%, and this may take place from 1 to 30 years.

The vast majority of oral leukoplakias will not turn malignant, however some subtypes hold greater risk than others. No interventions have been proven to reduce the risk of cancer developing in an area of leukoplakia, but people are generally advised to stop smoking and limit alcohol consumption to reduce the risk. Sometimes the white patch shrinks and eventually disappears after stopping smoking, but this may take up to a year. In many cases, areas of leukoplakia slowly expand and become whiter and thicken if smoking is not stopped.

It has been found that there is no treatment for leukoplakia that has been shown to be effective in preventing malignant transformation. Some treatments may lead to healing of leukoplakia, but do not prevent relapse of the lesion or malignant change.

Curcumin is a pleiotropic molecule possibly capable of interacting with molecular targets involved in inflammation. Curcumin modulates the inflammatory response by down-regulating the activity of cyclooxygenase-2, lipoxygenase and inducible nitric oxide synthase enzymes; and inhibits several other enzymes involved in inflammation mechanisms.

Study Design:

22 subjects showing severe symptoms of leucoplakia were selected for the study.

These subjects were advised to administer the pastilles of the present invention (containing 100 mg of turmeric extract) three times a day for 30 days. The follow up of the leukoplakia subjects was done twice in a month and the subjects were advised to maintain good oral health. The reduction in legion and inflammation was checked visually.

Conclusion:

Four subjects out of 22 showed complete recovery (100%) from leukoplakia, whereas the remaining subjects (18) showed significant improvement i.e. fourteen (14 out of 18) subjects showed 60 to 70% recovery from leukoplakia and four subjects (4 out of 18) showed 20 to 30% recovery from leukoplakia. These subjects (18) were advised to continue the treatment for one more month.

The applicant craves leave to submit the additional data related to ongoing clinical trials during the prosecution of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A soft pastille comprising:
   turmeric extract in an amount ranging from 0.1 wt. % to 20 wt. % of the mass of the pastille;
   at least one gelling agent in an amount ranging from 5 wt. % to 40 wt. % of the mass of the pastille;
   at least one plasticizer in an amount ranging from 30 wt. % to 70 wt. % of the mass of the pastille;
   at least one sweetener in an amount ranging from 0.05 wt. % to 10 wt. % of the mass of the pastille;
   at least one releasing agent in an amount ranging from 0.5 wt. % to 30 wt. % of the mass of the pastille;
   at least one preservative in an amount ranging from 0.05 wt. % to 2 wt. % of the mass of the pastille;
   at least one flavouring agent in an amount ranging from 0.01 wt. % to 5 wt. % of the mass of the pastille;
   water in an amount of ranging from 5 wt. % to 20 wt. % of the mass of the pastille, and
   optionally at least one pharmaceutically acceptable excipient,
   wherein the ratio of the gelling agent to the plasticizer is in a range of 1:2.5 to 1:3.3.

2. The pastille as claimed in claim 1, wherein the turmeric extract comprises 5 wt. % to 93 wt. % of curcuminoids, 5 to 30 wt. % of turmeric oil, and 1 to 10 wt. % of polysaccharides.

3. The pastille as claimed in claim 2, wherein the curcuminoids comprise 83 to 95 wt. % of curcumin, 2 to 7 wt. % of desmethoxycurcumin and 1 to 3 wt. % of bis-desmethoxycurcumin.

4. The pastille as claimed in claim 1, wherein the turmeric extract is at least one extract selected from the group consisting of alcoholic extract and hydro-alcoholic extract.

5. The pastille as claimed in claim 1, wherein the gelling agent is selected from the group consisting of gelatin, carrageenan and mixtures thereof.

6. The pastille as claimed in claim 1, wherein the plasticizer is selected from the group consisting of glycerine, sorbitol and mixtures thereof.

7. The pastille as claimed in claim 1, wherein the releasing agent is selected from the group consisting of lecithin, oil, starch and mixtures thereof.

8. The pastille as claimed in claim 1, wherein the sweetener is selected from the group consisting of stevia, aspartame, saccharin, sucralose, sucrose, dextrose, lactose and mixtures thereof.

9. The pastille as claimed in claim 1, wherein the preservative is selected from the group consisting of methyl paraben, propyl paraben, sodium methyl paraben, sodium propyl paraben, grape fruit seed extract, sodium benzoate and mixtures thereof.

10. The pastille as claimed in claim 1, wherein the flavouring agent is selected from the group consisting of menthol, vanillin, spearmint, peppermint, lemon, mint, strawberry, banana, pineapple, orange, raspberry, eucalyptol, fennel, cinnamon and mixtures thereof.

11. A process for the preparation of soft pastilles; said process comprising the following steps:
  a. introducing 30 to 70 wt. % of a plasticizer selected from the group consisting of glycerine, sorbitol and combinations thereof and water in a reactor followed by adding 5 to 40 wt. % of a gelling agent selected from the group consisting of gelatin, carrageenan and mixtures thereof and stirring to obtain a first mixture; heating said first mixture at a temperature ranging from 25° C. to 85° C., and admixing 0.5 to 30 wt. % of a releasing agent selected from the group consisting of lecithin, oil, starch and combinations thereof and optionally at least one pharmaceutically acceptable excipient to form a second mixture, wherein the ratio of the gelling agent to the plasticizer is in a range of 1:2.5 to 1:3.3;
  b. adding 0.1 to 20 wt. % of turmeric extract into glycerine to obtain slurry and mixing said slurry and the second mixture for 30 to 45 minutes at a speed of 1500 rpm to form a third mixture comprising partly dissolved and partly dispersed turmeric extract;
  c. incorporating 0.05 wt. % to 10 wt. % of at least one sweetener, 0.01 wt. % to 5 wt. % of at least one flavoring agent and 0.05 wt. % to 2 wt. % of at least one preservative into the third mixture to obtain a mass; and
  d. filling the mass into the preformed cavities of blister pack to obtain the pastilles.

12. The process as claimed in claim 11, wherein the process includes steps of collecting the mass in a container followed by cooling and solidification; transferring the solidified mass into a melter followed by adjusting the temperature of the mass in the range from 55° C. to 75° C. to obtain a melted mass; and passing the melted mass through an injector directly into the preformed cavities of blister pack.

13. The process as claimed in claim 11, wherein the sweetener is selected from the group consisting of stevia, aspartame, saccharin, sucralose, sucrose, dextrose, lactose and mixtures thereof; the preservative is selected from the group consisting of methyl paraben, propyl paraben, sodium methyl paraben, sodium propyl paraben, grape fruit seed extract, sodium benzoate and mixtures thereof; and the flavouring agent is selected from the group consisting of menthol, vanillin, peppermint, spearmint, lemon, mint, strawberry, banana, pineapple, orange, raspberry, eucalyptol, fennel, cinnamon and mixtures thereof.

14. The process as claimed in claim 11, wherein the turmeric extract comprises 5 wt. % to 93 wt. % of curcuminoids, 5 to 30 wt. % of turmeric oil and 1 to 10 wt. % of polysaccharides.

15. The process as claimed in claim 14, wherein the curcuminoids comprise 83 to 95 wt. % of curcumin, 2 to 7 wt. % of desmethoxycurcumin and 1 to 3 wt. % of bis-desmethoxycurcumin.

* * * * *